United States Patent

Tamari et al.

Patent Number: 4,957,509
Date of Patent: Sep. 18, 1990

[54] CERAMIC IMPLANT MATERIALS

[75] Inventors: Nobuyuki Tamari; Isao Kondoh; Nakoto Kinoshita, all of Ikeda, Japan

[73] Assignee: Agency of Industrial Science and Technology, Tokyo, Japan

[21] Appl. No.: 398,315

[22] Filed: Aug. 24, 1989

Related U.S. Application Data

[63] Continuation of Ser. No. 19,843, Feb. 27, 1987, abandoned.

[30] Foreign Application Priority Data

Feb. 28, 1986 [JP] Japan .................................. 61-44325

[51] Int. Cl.$^5$ .............................................. A61F 2/28
[52] U.S. Cl. .................................. 623/16; 433/201.1; 501/95
[58] Field of Search ........................ 433/201.1; 106/35; 623/16; 501/95; 264/60; 427/2; 423/266, 608

[56] References Cited

U.S. PATENT DOCUMENTS

| 4,278,630 | 7/1981 | Scheicher | 264/60 |
| 4,503,157 | 3/1985 | Hatahira | 501/95 X |
| 4,594,106 | 6/1986 | Tanaka et al. | 106/1.13 X |
| 4,639,356 | 1/1987 | O'Toole et al. | 423/266 |

FOREIGN PATENT DOCUMENTS 0012649  1/1983  Japan .................................. 623/16

Primary Examiner—Alan Cannon
Attorney, Agent, or Firm—Armstrong, Nikaido, Marmelstein, Kubovcik & Murray

[57] ABSTRACT

A ceramic implant material is disclosed, which comprises a porous zirconia or silicon nitride ceramic containing silicon carbide whiskers, the pores of which are filled with a material adapted to the tissue.

6 Claims, 1 Drawing Sheet

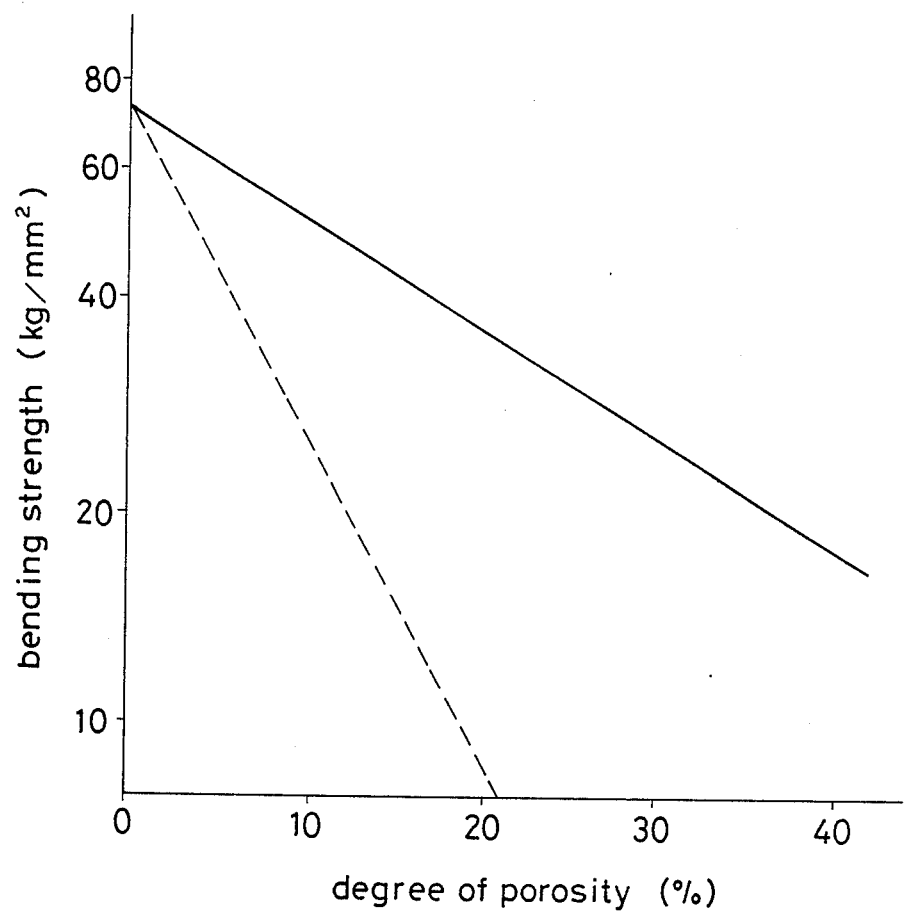

CERAMIC IMPLANT MATERIALS

This application is a continuation of application Ser. No. 019,843 filed Feb. 27, 1987, now abandoned.

BACKGROUND OF THE INVENTION

The present invention relates to ceramic implant materials which can be implanted in a living body, such as artificial roots of teeth or artificial bones.

Ceramic materials are characterized by the fact that rejection of them by a living body is only slight and they are not corroded easily and, therefore, the use of them as implant materials such as artificial roots of teeth or artificial bones is expected. Thus, the use of various ceramic materials as implant materials has been studied and a variety of clinical examples wherein they are used have been reported since about 15 years ago.

Single-crystal or polycrystalline alumina, for example, is a material against which the rejection by a living body is slight, and investigations have been made on the use of it as the implant material. However, since the tissue does not easily adapt itself to said alumina and since the strength and hardness of the alumina are excessively high, the tissue in contact with the aluminous ceramic is often inflamed or abraded.

Polycrystalline silicon nitrides and zirconia which are attracting attention recently also have the defects that the tissue does not adapt easily itself to them and they do not adhere to the tissue and, therefore, no interference layer can be formed between them. Consequently, when a strong impact is applied to them, the tissue is inflamed.

On the other hand, though calcium phosphates such as hydroxyapatite or tricalcium phosphate comprising components very close to those constituting natural bones have excellent adaptability to the tissue, their strength and toughness to a sudden impact or stress applied when they are used as the artificial roots of teeth or artificial bones are yet insufficient. They are thus unsuitable for use as the implant materials.

Under these circumstances, investigations were made on composite materials comprising a core made of an aluminous ceramic and a surface layer made of hydroxyapatite or tricalcium phosphate to which the tissue easily adapts itself. However, these composite materials require considerable labor and steps in the preparation thereof and they are yet unsatisfactory for use as the implant ceramics, since the adhesion between the calcium phosphate constituting the surface layer and the aluminous ceramic constituting the core is insufficient.

SUMMARY OF THE INVENTION

An object of the present invention is to provide a ceramic implant material easily adaptable to living tissues, having an excellent strength and suitable for use as artificial roots of teeth or artificial bones.

Another object of the invention is to provide a ceramic impact material capable of forming a surrounding shock-absorbing zone to prevent an inflammation after being embedded in the tissue.

The objects of the present invention can be attained by providing a ceramic material comprising a matrix made of porous zirconia or silicon nitride ceramic containing silicon carbide whiskers, the pores being filled with a material to which the tissue of a living body is adaptable itself.

BRIEF DESCRIPTION OF THE DRAWING

The drawing is a graph showing the relationship between the bending strength and the degree of porosity of a silicon nitride ceramic containing silicon carbide whiskers (solid line) and silicon nitride ceramic free of silicon carbide whiskers (broken line).

THE PREFERRED EMBODIMENTS

The matrix of the ceramic material of the present invention comprises a porous zirconia ceramic or silicon nitride ceramic.

The ceramic matrix contains silicon carbide whiskers.

The ceramic matrix is made porous so that the pores are filled with materials adapted to the tissue and the silicon carbide whiskers are contained therein so as to prevent the reduction of the strength of the ceramic matrix due to the presence of the pores.

Though the zirconia ceramics may comprise zirconia alone, it is preferred to use a partially stabilized zirconia containing further yttria, magnesia, etc. so as to further increase the strength.

As pure zirconia is cooled from high temperature to ambient temperature, its crystalline system changes from the cubic system to a tetragonal system and then to a monoclinic system. Particularly in the phase transition from the tetragonal system to the monoclinic system, the volume is expanded by about 5% and cracks are formed in the sintered compact.

The phase transition from the tetragonal system into the monoclinic system can be controlled to keep the cubic or tetragonal system by adding a stabilizer such as CaO, MgO or $Y_2O_3$ to $ZrO_2$ at ambient temperature. Zirconia exclusively composed of the cubic system obtained by adding a sufficient amount of the stabilizer is called fully stabilized zirconia (FSZ), while zirconia composed of cubic and tetragonal or monoclinic systems, stabilized with a stabilizer such as MgO or $Y_2O_3$ in an amount of as small as 1 to 4 molar % is called partially stabilized zirconia (PSZ).

As compared with FSZ, PSZ has superior mechanical properties such as strength, and toughness.

As for the preparation of the silicon nitride ceramics, silicon nitride powder is formed by the reactions of $Si+N_2$ and $SiO_2+C+N_2$. This powder is mixed with about 5% of MgO and 10 to 30% of $(Al_2O_3+Y_2O_3)$ and the mixture is sintered by hot-pressing at 1650 to 1750° C. in a vacuum or in a nitrogen atmosphere under pressure.

The zirconia ceramics and silicon nitride ceramics have a strength equivalent to or higher than that of aluminous ceramics now available as implant materials on the market and, in addition, the rejection of the living tissue against them which occurs when they are implanted in the tissue is only slight. Thus, these ceramics have suitable properties for use as the implant materials.

The porosity of the ceramic matrix is represented by the degree of porosity. Though a high degree of porosity is preferred for filling the matrix with a large amount of a material adapted to the tissue, the strength of the ceramics is reduced when the degree of porosity is excessively high. The degree of porosity of the ceramic material of the present invention is controlled so that the strength thereof will be at least equal to that of living bones (10 to 15 kg/mm$^2$).

The strength varies also depending on the silicon carbide whisker content and the porosity is usually in the range of 15 to 40%.

Though the size of the pores is not particularly limited, the diameter thereof is preferably about 5 to 100 $\mu$m and still preferably about 20 to 60 $\mu$m from the viewpoint of the balance between the strength of the ceramic and easiness of impregnation thereof with the filler.

A preferred amount of the silicon carbide whiskers in the ceramic matrix is usually about 10 to 45 volume % based on the ceramic body excluding the pores.

When the amount of the silicon carbide whiskers is less than 10 vol. %, no sufficient effect of maintaining the strength of the porous ceramic can be obtained and, on the contrary, when it exceeds 45 vol. %, the pores are formed in an excessive amount in the sintered compact of the ceramic to reduce the strength of the sintered compact unfavorably.

FIG. 1 shows the relationship between the degree of porosity and bending strength of the silicon nitride ceramic free of the silicon carbide whiskers (broken line in FIG. 1) and that between the degree of porosity and bending strength of the silicon nitride ceramic containing the silicon carbide whiskers (solid line in FIG. 1). It can be understood from FIG. 1 that the bending strength of the porous ceramic is improved remarkably by incorporating silicon carbide whiskers therein.

Though the impregnation can be effected by immersing the porous ceramic material in an aqueous solution or slurry, satisfactory impregnation is often impossible by this process. A preferred process comprises reducing the pressure in the pores of the ceramic material and impregnating the material with the aqueous solution or slurry. Another preferred process comprises introducing the aqueous solution or slurry into the pores of the ceramic material under pressure.

The concentration of the aqueous solution or slurry of the materials adapted to the tissue is preferably high so that the pores of the ceramic are filled sufficiently with the materials. Collagens and mucopolysaccharides are used preferably in the form of an aqueous solution thereof having a concentration ranging from about 30 wt. % to saturation. Calcium phosphates are used preferably in the form of a slurry having a concentration of at least 10 wt. % and as high as possible. When the concentration of the aqueous solution or slurry is below said range, the amount of the material adapted to the tissue in the porous ceramic material is insufficient. When such a ceramic material is embedded in the tissue, an effective fresh bone or tendon can not be easily formed unfavorably, since the adaptability is insufficient. When the slurry is used, the particle size of the material adapted to the tissue is preferably as small as less than 10 $\mu$m, particularly less than 1 $\mu$m, so that the pores of the ceramic can be fully charged with it.

The material adapted to the tissue may be any of those which exhibit an excellent adaptability to the tissue when the ceramic having the pores filled with them is embedded in the tissue and which are capable of accelerating the formation of a fresh bone or tendon. Examples of the materials adapted to the tissue include collagen; mucosaccharides such as chondroitin, heparin and chitin; and calcium phosphates such as hydroxyapatite, tricalcium phosphate, tetracalcium phosphate and octacalcium phosphate. They can be used either alone or in the form of a mixture of them. The ceramic can be impregnated with these materials by, for example, filling the pores of the ceramic with them in the form of an aqueous solution or slurry thereof and then drying and solidifying the same.

Now, the description will be made on the processes for the preparation of the ceramic material of the present invention.

The zirconia ceramic material or silicon nitride ceramic material is mixed homogeneously with the silicon carbide whiskers.

The zirconia ceramic material and silicon nitride ceramic material are prepared from zirconia, yttria, magnesia, silicon nitride, etc. generally available on the market.

The particle size of these starting materials is preferably as small as possible, e.g. less than 1 $\mu$m, from the viewpoint of the degree of sintering and strength. The purity of them is preferably as high as possible. The silicon nitride ceramic contains usually about 5 to 15 molar % of magnesia, alumina, a rare earth oxide or the like as a sintering aid. These sintering aids have preferably a high purity and a small particle diameter.

The silicon carbide whiskers usually available on the market can be used. They have preferably a high dispersibility. For example, those having a length of about 30 to 100 $\mu$m and a diameter of about 0.1 to 1.0 $\mu$m can be used.

The obtained mixture of the starting materials is then shaped and calcined to obtain a porous ceramic.

The mixture of the starting materials can be shaped and sintered by any of processes employed usually for the ceramic materials, such as hot pressing process, atmospheric pressure sintering process and hot isostatic pressing process.

In the hot pressing process, the shaped product is calcined under conditions comprising, for example, a pressure of about 100 to 300 kg/cm$^2$ and a temperature of about 1200° to 1400° C. for the zirconia ceramic or about 1600° to 1800° C. for the silicon nitride ceramic for about 20 to 60 min to obtain a porous ceramic.

In the atmospheric pressure sintering process, the zirconia ceramic is calcined at about 1350° to 1500° C. and the silicon nitride ceramic is calcined at about 1700° to 1900° C. for about 60 to 120 min. Generally, when the calcination temperature is above said range the obtained sintered compact has too high a density to be filled with the material adapted to the tissue sufficiently and, on the contrary, when it is below said range, the degree of porosity of the sintered compact is too high and the strength thereof is reduced.

Then, the pores of the obtained porous sintered compact are filled with the material adapted to the tissue to obtain the ceramic material of the present invention. The filling can be effected by impregnating the ceramic with the aqueous solution or slurry of the material adapted to the tissue and then drying it to obtain a solid product.

The ceramic material of the present invention prepared as described above has a sufficient strength which is at least equal to that of living bones, i.e. at least 10 to 15 kg/mm$^2$. Since the material adapted to the tissue is filled in the pores, a fresh bone, tendon, etc. are formed around the ceramic after embedding it in the tissue. Thus, the ceramic material embedded in the tissue has a strength sufficiently resistant to a sudden impact and a sufficient shock-absorbing zone is formed to prevent inflammation. Thus, the ceramic of the present invention is quite useful as a implant material such as an artificial root of a tooth or artificial bone.

The following examples will further illustrate the present invention.

EXAMPLE 1

Partially stabilized zirconia powder (particle diameter: 0.3 μm) containing 3 molar % of yttrium oxide was mixed with silicon carbide whiskers (diameter: 0.5 μm, length: 50 to 100 μm) in water for 1 h to obtain a dispersion, which was then dried. The obtained mixture was shaped by hot pressing and sintered at 1300° C. under 300 kg/cm$^2$ for 30 min to obtain a ceramic having a relative density of 73% (degree of porosity: 27%) and a silicon carbide whisker content of 30 vol. %. Test pieces having a size of 3×3×30 mm$^3$ were cut out of the product and subjected to a three-point bending test under conditions comprising a span of 20 mm and a loading rate of 0.5 mm/min. The product had a strength of 32 kg/mm$^2$.

The porous silicon carbide whisker-zirconia ceramic obtained as above was immersed in a 50% aqueous solution of collagen fibers to fill the pores with the collagen and then it was dried to solidify the collagen and to obtain a ceramic implant material.

EXAMPLE 2:

The same partially stabilized zirconia powder and silicon carbide whiskers as in Example 1 were mixed together in a volume ratio of 60:40. The mixture was subjected to cold isostatic pressing under a pressure of 3000 kg/cm$^2$. The obtained shaped product was calcined at 1500° C. in an argon atmosphere for 90 min to obtain a ceramic having a relative density of 68% (degree of porosity: 32%) and a bending strength of 25 kg/mm$^2$.

The porous silicon carbide whisker-zirconia ceramic prepared as above was placed in a vacuum, then immersed in a 50% slurry of hydroxyapatite powder (particle diameter: 0.1 μm) and then dried to obtain a ceramic implant material.

EXAMPLE 3:

The same silicon carbide whiskers as in Example 1 were added to silicon nitride powder (particle diameter: 0.7 μm) containing 15 molar % of magnesia as the sintering aid. The mixture was hot-pressed at 1750° C. under 200 kg/cm$^2$ for 20 min. The obtained ceramic had a silicon carbide whisker content of 20 vol. %, a relative density of 77% (degree of porosity: 23%) and a bending strength of 33 kg/mm$^2$.

The porous silicon carbide whisker-silicon nitride ceramic prepared as above was immersed in a 70% aqueous chondroitin solution and then dried to obtain a ceramic implant material.

EXAMPLE 4:

Silicon carbide whiskers (diameter: 0.5 μm, length: 30 to 50 μm) were added to silicon nitride powder (particle diameter: 0.7 μm) containing 7.5 molar % of yttrium oxide and 7.5 molar % of lanthanum oxide as sintering aids and the mixture was subjected to cold isostatic pressing under a pressure of 3,000 kg/cm$^2$ and then calcined at 1850° C. in a nitrogen atmosphere of 10 atm for 60 min. The obtained ceramic had a silicon carbide whisker content of 36 vol. %, a relative density of 69% (degree of porosity of 31%) and a bending strength of 24 kg/mm$^2$.

The porous silicon carbide whisker-silicon nitride ceramic prepared as above was immersed in a 70% slurry of a mixture of tricalcium phosphate and collagen (weight ratio of tricalcium phosphate to collagen of 1:1) and a pressure was applied thereto to impregnate the ceramic with the slurry. After drying, a ceramic implant material was obtained.

CLINICAL EXPERIMENTS

Clinical experiments were effected by embedding the ceramic implant materials prepared in Examples 1 to 4, the porous ceramic prepared in Example 1 but not impregnated with the collagen (Comparative Example 1) and the porous ceramic prepared in Example 4 but not impregnated with the slurry of the mixture of tricalcium phosphate and collagen (Comparative Example 2) in the lower jaws of dogs. The ceramic materials of Examples 1 to 4 were adaptable to the tissues (epithelium of the mucous membrane and bone tissues) and firmly adhered thereto but the ceramic materials of Comparative Examples 1 and 2 did not adhere to the tissue.

We claim:

1. A ceramic implant consisting essentially of a matrix comprising zirconia or silicon nitride ceramic, wherein the matrix is a porous one having a porosity of 15 to 40%, contains a substance adapted to living tissue in the pores thereof, and contains silicon carbide whiskers in the amount of 10 to 45% based on the volume of the matrix excluding the volume of the pores therein, wherein said substance adapted to living tissue is at least one compound selected from the group consisting of collagens, mucopolysaccharides and calcium phosphates, this substance being deposited in the pores of said matrix by being applied in the form of an aqueous solution or slurry thereof and then being dried and solidified, and wherein the ceramic matrix, in the case of zirconia, is in a phase selected from the group consisting of cubic, tetragonal and monoclinic, and, in the case of silicon nitride, is in a phase selected from the group consisting of trigonal and hexagonal.

2. The ceramic implant material according to claim 1 wherein said pores in the matrix have a diameter of 5 to 100 μm.

3. The ceramic implant material according to claim 1, wherein the substance adapted to living tissue is at least one member selected from the group consisting of chondroitin, heparin and chitin.

4. The ceramic implant material according to claim 1, wherein the substrate adapted for living tissue is at least one member selected from the group consisting of hydroxyapatite, tricalcium phosphate, tetracalcium phosphate and octacalcium phosphate.

5. The ceramic implant material according to claim 1 wherein said matrix comprises zirconia which is partially stabilized by a stabilizer.

6. The ceramic implant material according to claim 5, wherein said stabilizer is at least one member selected from the group consisting of CaO, MgO and Y$_2$O$_3$.

* * * * *